United States Patent
Chappuis

(10) Patent No.: US 7,534,245 B2
(45) Date of Patent: May 19, 2009

(54) FLEXIBLE TAP APPARATUS AND METHOD OF USE

(76) Inventor: James L. Chappuis, 3170 Lakeridge Dr., Marietta, GA (US) 30067

( * ) Notice: Subject to any disclaimer, the term of this patent is extended or adjusted under 35 U.S.C. 154(b) by 0 days.

(21) Appl. No.: 10/725,683

(22) Filed: Dec. 2, 2003

(65) Prior Publication Data
US 2004/0122432 A1 Jun. 24, 2004

Related U.S. Application Data

(60) Provisional application No. 60/430,247, filed on Dec. 2, 2002.

(51) Int. Cl.
*A61B 17/00* (2006.01)
(52) U.S. Cl. .......................................... 606/79
(58) Field of Classification Search ................. 606/53, 606/79, 80, 72, 73; 433/144; 408/189, 203.5, 408/205, 222, 198, 57, 59; 604/19, 22, 41, 604/43, 44
See application file for complete search history.

(56) References Cited

U.S. PATENT DOCUMENTS

| | | | | |
|---|---|---|---|---|
| 3,626,928 A * | 12/1971 | Barringer et al. | ............ | 600/563 |
| 3,636,940 A * | 1/1972 | Gravlee | ...................... | 600/563 |
| 4,751,922 A * | 6/1988 | DiPietropolo | ................ | 606/80 |
| 4,762,444 A * | 8/1988 | Mena | .......................... | 408/59 |
| 4,790,813 A * | 12/1988 | Kensey | ........................ | 604/22 |
| 5,047,040 A * | 9/1991 | Simpson et al. | ............. | 606/159 |
| 5,129,901 A * | 7/1992 | Decoste | ........................ | 606/65 |
| 5,171,277 A * | 12/1992 | Roger | .......................... | 606/86 |
| 5,242,443 A * | 9/1993 | Kambin | ........................ | 606/60 |
| 5,269,751 A * | 12/1993 | Kaliman et al. | ............... | 604/22 |
| 5,269,785 A * | 12/1993 | Bonutti | ........................ | 606/80 |
| 5,358,485 A * | 10/1994 | Vance et al. | .................. | 604/22 |
| 5,409,489 A * | 4/1995 | Sioufi | .......................... | 606/80 |
| 5,499,984 A * | 3/1996 | Steiner et al. | ................. | 606/80 |
| 5,944,686 A * | 8/1999 | Patterson et al. | .............. | 604/22 |
| 6,019,776 A * | 2/2000 | Preissman et al. | ........... | 606/185 |
| 6,048,343 A * | 4/2000 | Mathis et al. | ............... | 606/916 |
| 6,053,918 A * | 4/2000 | Spievack | ...................... | 606/64 |
| 6,293,952 B1 * | 9/2001 | Brosens et al. | .............. | 606/119 |
| 6,371,935 B1 * | 4/2002 | Macoviak et al. | ............. | 604/43 |
| 6,375,635 B1 * | 4/2002 | Moutafis et al. | ............... | 604/43 |
| 6,419,678 B1 * | 7/2002 | Asfora | ......................... | 606/96 |
| 6,494,859 B2 * | 12/2002 | Love et al. | ..................... | 604/28 |
| 6,524,318 B1 * | 2/2003 | Longhini et al. | .............. | 606/86 |
| 6,588,386 B2 * | 7/2003 | Kong | ....................... | 123/90.16 |
| 6,607,530 B1 * | 8/2003 | Carl et al. | ...................... | 606/61 |
| 6,635,059 B2 * | 10/2003 | Randall et al. | ................ | 606/73 |
| 6,652,532 B2 * | 11/2003 | Bonutti | ........................ | 606/80 |

(Continued)

*Primary Examiner*—Anu Ramana
(74) *Attorney, Agent, or Firm*—Thomas, Kayden, Horstemeyer & Risley, LLP.

(57) ABSTRACT

A flexible tap apparatus system comprises a first flexible tap apparatus member having a shaft having an upper shaft portion and a lower shaft portion. The upper shaft portion comprises ridges and the lower shaft portion has a substantially smooth surface. The shaft of the first flexible tap apparatus member comprises a first set of dimensions. The system further comprises a second flexible tap apparatus member having a shaft having an upper shaft portion and a lower shaft portion. The upper shaft portion comprises ridges and the lower shaft portion has a substantially smooth surface. The shaft of the second flexible tap apparatus member comprises a second set of dimensions. The first set of dimensions differs from the second set of dimensions. A method of use is also provided.

4 Claims, 3 Drawing Sheets

U.S. PATENT DOCUMENTS

| | | |
|---|---|---|
| 6,669,680 B1 * | 12/2003 | Macoviak et al. ........... 604/509 |
| 6,716,216 B1 * | 4/2004 | Boucher et al. ............... 606/86 |
| 6,746,451 B2 * | 6/2004 | Middleton et al. ............ 606/79 |
| 6,755,831 B2 * | 6/2004 | Putnam et al. ................ 606/69 |
| 6,918,908 B2 * | 7/2005 | Bonner et al. ................. 606/41 |
| 2002/0156530 A1 * | 10/2002 | Lambrecht et al. ....... 623/17.16 |

* cited by examiner

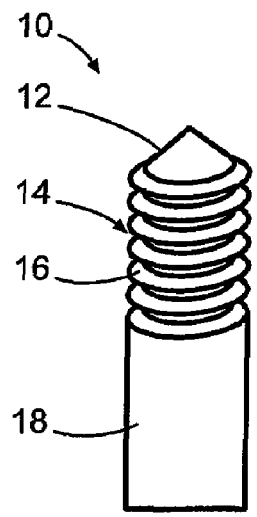
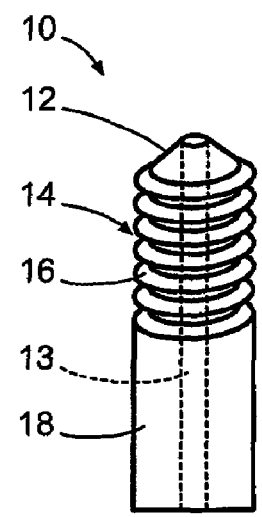
FIG. 1     FIG. 2
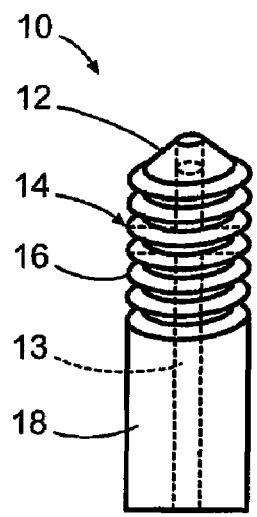
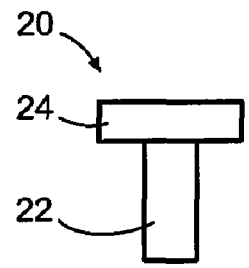
FIG. 3     FIG. 4

FLEXIBLE TAP APPARATUS AND METHOD OF USE

CROSS-REFERENCE TO RELATED APPLICATION

This application claims priority to copending U.S. provisional application entitled, "Flexible Tap Apparatus and Method of Use," having Ser. No. 60/430,247, filed on Dec. 2, 2002, which is entirely incorporated herein by reference.

TECHNICAL FIELD

The present invention generally relates to systems, devices, and methods related to the insertion of pedicle screws in a vertebral body, and more particularly is related to a flexible tap apparatus and method of use.

BACKGROUND OF THE INVENTION

Skeletal structures are formed of bones and adjoining structures which include cartilage, for instance. For various reasons, these skeletal structures may require artificial support or stabilization. For example, the human spine is composed of a column of thirty-three bones, called vertebrae, and their adjoining structures. The twenty-four vertebrae nearest the head are separate bones capable of individual movement and generally are connected by anterior and posterior longitudinal ligaments and by discs of fibrocartilage, called intervertbral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of these vertebrae include a vertebral body and a dorsal arch that enclose an opening, called the vertebral foramen, through which the spinal cord and spinal nerves pass. The remaining nine vertebrae located below the lumbar spine are fused to form the sacrum and the coccyx and are incapable of individual movement.

Pedicle screws can be used in spinal surgeries for various applications such as fusion of vertebra, correction of spinal deformities, and treatment of fractures. In these uses, the pedicle screw is inserted into the vertebral body via the narrowed pillar portion of the spine, the pedicle, and extends through the pedicle when properly positioned. The pedicle comprises a cancellous or spongy, porous, bone structure. The introduction of a pedicle screw to a vertebral body can result in various complications, including but not limited to the "break-out" of the pedicle screw through the pedicle wall. Where the pedicle screw is implemented in the thoracic spine, injury to the thoracic spinal cord can occur. A lateral break-out can result in damages to surrounding blood vessels and other structures. In order to minimize the likelihood of such complications surgeons often use a pedicle screw that is greatly reduced in size as compared to the pedicle such as to provide a safety margin in the insertion.

However, particularly in the thoracic and lumbar spine, eighty percent of the pull out strength is obtained by the fit of the pedicle screw into the pedicle. As such, the maximum size pedicle screw for the size pedicle lends the maximum pull out strength. Insertion of rigid members, such the pedicle screw and a typical pedicle tap, into a pedicle that are of such a desired size can result in perforation of the pedicle.

Thus, a heretofore unaddressed need exists in the industry to address the aforementioned deficiencies and inadequacies.

SUMMARY OF THE INVENTION

Preferred embodiments of the present invention provide a flexible tap apparatus system. Briefly described, in architecture, one embodiment of the system comprises a first flexible tap apparatus member having a shaft having an upper shaft portion and a lower shaft portion. The upper shaft portion comprises ridges and the lower shaft portion has a substantially smooth surface. The shaft of the first flexible tap apparatus member comprises a first set of dimensions. The system further comprises a second flexible tap apparatus member having a shaft having an upper shaft portion and a lower shaft portion. The upper shaft portion comprises ridges and the lower shaft portion has a substantially smooth surface. The shaft of the second flexible tap apparatus member comprises a second set of dimensions. The first set of dimensions differs from the second set of dimensions.

Preferred embodiments of the present invention can also be viewed as providing methods of creating a passage in tissue. In this regard, one embodiment of such a method, among others, can be broadly summarized by the following steps: providing a flexible tap apparatus system comprising; a first flexible tap apparatus member as disclosed above; and a second flexible tap apparatus member, as disclosed above; engaging the first flexible tap apparatus member into the tissue; disengaging the first flexible tap apparatus member from the tissue; and engaging the second flexible tap apparatus member into the tissue.

Other systems, methods, features and advantages of the present invention will be or become apparent to one with skill in the art upon examination of the following drawings and detailed description. It is intended that all such additional systems, methods, features, and advantages be included within this description, be within the scope of the present invention, and be protected b the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 1 illustrates a front view of an embodiment of a flexible tap apparatus member of the present invention.

FIG. 2 illustrates a front view of another embodiment of a flexible tap apparatus member of the present invention illustrated in FIG. 1.

FIG. 3 illustrates a front view of another embodiment of a flexible tap apparatus member of the present invention illustrated in FIG. 1.

FIG. 4 illustrates a planar view of an embodiment of a handle of the present invention.

DETAILED DESCRIPTION OF THE PREFERRED EMBODIMENTS

Figure 5:
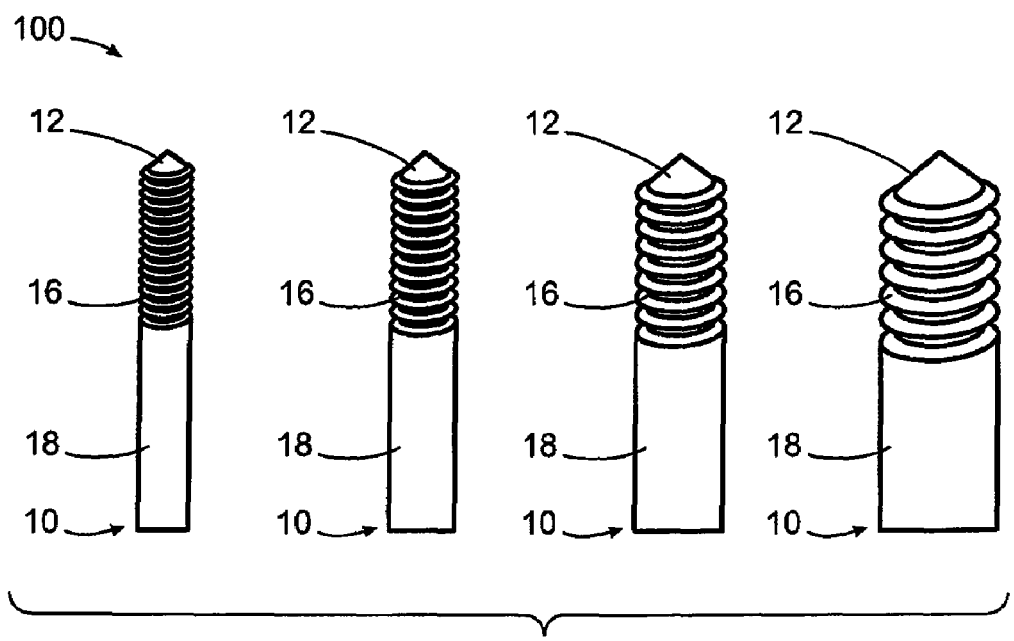
FIG. 5 illustrates a front view of an embodiment of a pedicle tap apparatus system of the present invention.

FIG. 1 illustrates one preferred embodiment of a flexible tap apparatus member 10. The flexible tap apparatus member 10 comprises a shaft 14 having an upper shaft portion 16 and a lower shaft portion 18. The upper shaft portion 16 comprises a threaded surface terminating at a head 12. The threaded surface is adapted to prepare a pedicle to receive a threaded member, such as a pedicle screw, or the like. The flexible tap apparatus member 10 has a substantially circular cross-section. The head 12 is preferably substantially conical in shape for facilitating insertion into tissue with which the tap apparatus member 10 in engaged during use. The lower shaft portion 18 comprises a substantially smooth surface. It is desirable that both the upper shaft portion 16 and the lower shaft portion 18 are flexible to reduce the likelihood of breakout from a pedicle. The shaft portion 18 can be flexible in any suitable direction, such as from side-to-side, or to alter length of the tap apparatus member 10. The tap apparatus member 10 can be made of any suitable material, including but not limited to titanium.

FIG. 2 illustrates another embodiment of the flexible tap apparatus member 10. More specifically, the shaft 14 is cannulated having a passage 13 disposed axially therethrough. The passage 13 extends the entire length of the shaft 14. The passage 13 is arranged and configured to engage a guide pin 30 (FIG. 7) for alignment during use, which is discussed in greater detail herein.

The passage 13 can also be used to introduce dye to the tissue engaged by the tap apparatus member 10 during use. Among other benefits, use of dye aids in ensuring that the tap apparatus member 10 is positioned as desired in the tissue, such as in the pedicle 202.

FIG. 3 illustrates another embodiment of the flexible tap apparatus member 10. The tap apparatus member 10 is cannulated with a passage 13 disposed axially threrethrough. FIG. 3 illustrates the passage 13 extending over ⅔ the length of the shaft 14. It should be understood, however, that the passage 13 can extend the entire length of the shaft 14 or any desired portion of the length of the shaft 14. The tap apparatus member 10 also includes a plurality of lateral passages 15. Each of the lateral passages 15 extends from the center passage 13 through an outer wall of the member 10. The lateral passages 15 can be disposed at any angle with respect to the passage 13. The lateral passages 15 are arranged and configured to communicate dye, or any suitable material, desired to be distributed into the tissue with which the tap apparatus member 10 is engaged during use. Such desired material is introduced to the lateral passages 15 via the axial passage 13. Although a plurality of lateral passages 15 are disclosed herein, it should be understood that any number of lateral passages 15 can be disposed in the tap apparatus member 10 extending from the passage 13.

FIG. 4 illustrates an embodiment of a handle 20 for use with a flexible tap apparatus member 10. The handle 20 comprises an engagement portion 22 and a grip 24. The handle 20 is arranged and configured to interchangeably receive tap apparatus members 10 of various dimensions. The lower shaft portion 18 of the tap apparatus member 10 is releasably received by the engagement portion 22 of the handle 20 such that the upper shaft portion 16 extends away from the grip 24 of the handle 20. Upon engagement of the apparatus member 10 with the handle 20, the handle 20 is used to facilitate applying pressure to the tap apparatus member 10 and to manipulate and twist the tap apparatus member 10 into the desired tissue. The handle 20 can be fixed to the shaft 14 by a threaded screw insertion, a snap-fit insertion, or any suitable fitting. The grip 24 is illustrated herein as being disposed at approximately a 90° angle to the engagement portion 22, however, it should be understood that any suitable configuration of the grip 24 in relation to the engagement portion 22 is within the spirit of the present invention.

FIG. 5 illustrates a plurality of flexible tap apparatus members 10 comprising a flexible tap apparatus system 100. Each of the flexible tap apparatus members 10 exhibit similar structure and differ primarily by at least one dimension thereof. Although the tap apparatus member 10 is disclosed herein as being of a particular variable dimension, the tap apparatus members 10 comprising a system 100 can differ between each other in a variety of aspects without departing from the spirit of the present invention. As an example, the plurality of tap apparatus members 10 can range from having a shaft 14 of 2 mm diameter gradually increasing to a tap apparatus member 10 having an 8 mm diameter shaft 14, where each shaft 14 increases in diameter by, for example, 2 mm. As further example, the length of the apparatus can also vary between each apparatus member 10 comprising the system 100. For example, the tap apparatus members 10 can expand from a 2.5 mm length to a 5.0 mm length in increments of 0.5 mm. The system 100 can also comprise a plurality of apparatus members 10 increasing in a combination of dimensions. Furthermore, although four tap apparatus members 10 are illustrated as comprising the system 100, it should be understood that any number of tap apparatus members 10 might be implemented.

Figure 6:
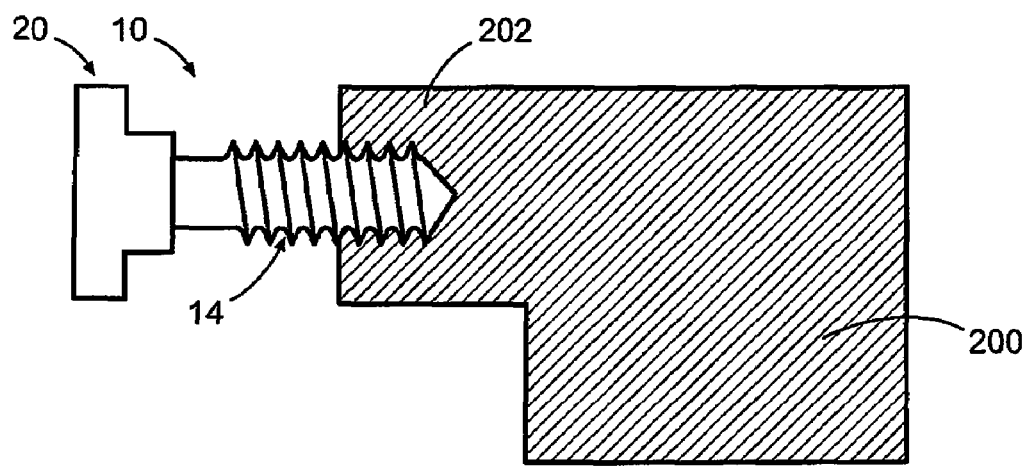
FIG. 6 illustrates a cross-section view of a method of use of the embodiment of the flexible tap apparatus member illustrated in FIG. 1.

FIG. 6 illustrates one method of use of the flexible tap apparatus member 10 illustrated in FIG. 1. A flexible tap apparatus member 10 engages a pedicle 202 of a vertebral body 200. The handle 20 is releasably fixed to the lower shaft portion 18 of the tap apparatus member 10 at the engagement portion 22 of the handle 20. The tap apparatus member 10 is introduced to the pedicle 202 by applying pressure to the handle 20 at the grip 24. Tap apparatus members 10 increasing in dimension as desired are successively introduced in a similar manner. As each tap apparatus member 10 is introduced to the pedicle 202 the passage being created in the pedicle 202 is slightly broadened and/or deepened. In one application, the passage in the pedicle 202 is broadened until the relatively soft cancellous bone of the pedicle is gone and an inner portion of the cortical pedicle sleeve is engaged. This contact is often signified to the user by a "chatter" sound as the tap 10 engages the relatively harder cortical pedicle sleeve or a vibration.

Figure 7:
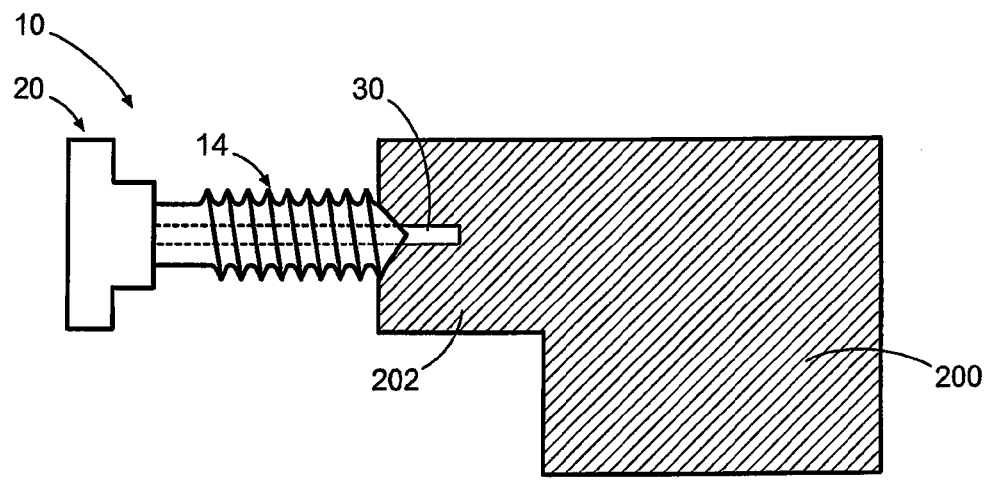
FIG. 7 illustrates a cross-section view of a method of use of the embodiment of the flexible tap apparatus member illustrated in FIG. 2.

FIG. 7 illustrates a method of use employing the tap apparatus member 10 illustrated in FIG. 2. The handle 20 is releasably fixed to the lower shaft portion 18 of the tap apparatus member 10 at the engagement portion 22. A guide pin 30 is disposed in a desired position in the pedicle 202. The flexible tap apparatus member 10 having a passage 13 disposed axially therethough engages the guide pin 30 at the passage 13. Pressure is applied to the tap apparatus member 10 via the grip 24 of the handle 20. Tap apparatus members 10 increasing in dimension as desired are successively introduced in a similar manner, slightly broadening and/or deepening the passage being created in the pedicle 202 with the use of each tap apparatus member 10. Upon achieving the desired passage dimensions in the pedicle 202, the last used tap apparatus member 10 is removed from the tissue as well as the guide pin 30.

Figure 7A:
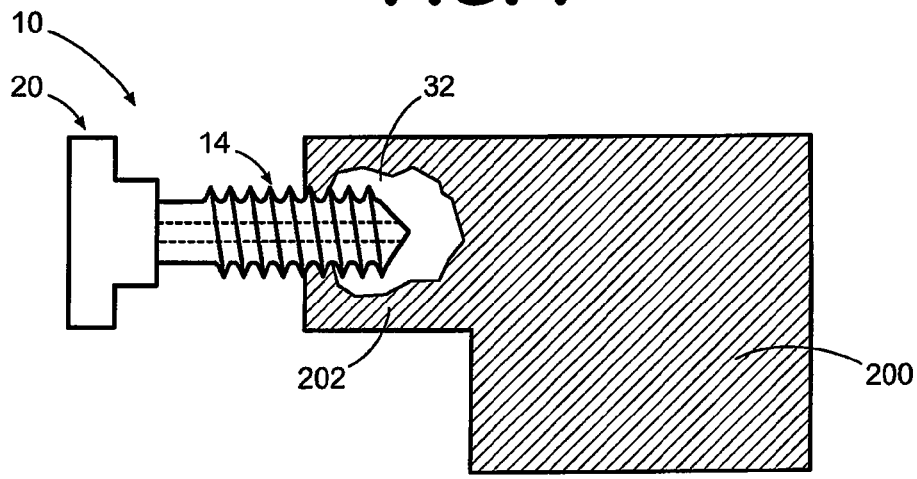
FIG. 7A illustrates a cross-section view of another method of use of the embodiment of the flexible tap apparatus member illustrated in FIG. 2.

FIG. 7A illustrates another method of use of the tap apparatus member 10 illustrated in FIG. 2. The flexible tap apparatus member 10 engages a pedicle 202 of a vertebral body 200 without the alignment of a guide pin 30. The handle 20 is releasably fixed to the lower shaft portion 18 of the tap apparatus member 10 at the engagement portion 22 of the handle 20. The tap apparatus member 10 is introduced to the pedicle 202 by applying pressure to the handle 20 at the grip 24. Tap apparatus members 10 increasing in dimension as desired are successively introduced in a similar manner. As each tap apparatus member 10 is introduced to the pedicle 202 the passage in the pedicle 202 is slightly broadened and/or deepened. At any step in this method of use, dye 32 or another desired material, is introduced into the passage 13 disposed axially through the tap apparatus member 10. Dye 32 can be introduced by removal of the handle 20 from the tap apparatus member 10 thereby exposing the opening of the passage 13. In another embodiment, the handle 20 may have a passage (not shown) disposed therethrough arranged and configured to align with the passage 13 of the tap apparatus member 10 through which dye, or any desired material, can be introduced.

Dye 32 can also be introduced to the tissue where a guide pin 30 is implemented to align the tap apparatus member 10. In this method of use, the guide pin 30 is removed and dye is introduced to the tissue via the passage 13. The guide pin 30 can be removed by first removing the handle 20 and extracting the guide pin through the passage 13 without disengaging the tap apparatus member 10 from the tissue. Dye 32 can then be introduced to the tissue via the passage 13.

In another method, the guide pin 30 is removed by removing both the handle 20 and the tap apparatus member 10 from the tissue. The guide pin 30 is then removed and a tap apparatus member 10 is reintroduced to the tissue without a guide pin 30 in position. Dye 32 is introduced to the tissue via the unobstructed passage 13.

In another method, the handle 20 comprises a passage (not shown) disposed therethrough and arranged and configured to align with the passage 13 of the tap apparatus member 10. The guide pin 30 is removed by extraction through the passage 13 of the tap apparatus member 10 as well as through a passage (not shown) disposed in the handle. Similarly, upon removal of the guide pin 30, dye 32 can be introduced to the tissue via the passage (not shown) disposed in the handle 20 and the passage 13 of the tap apparatus member 10.

Figure 8:
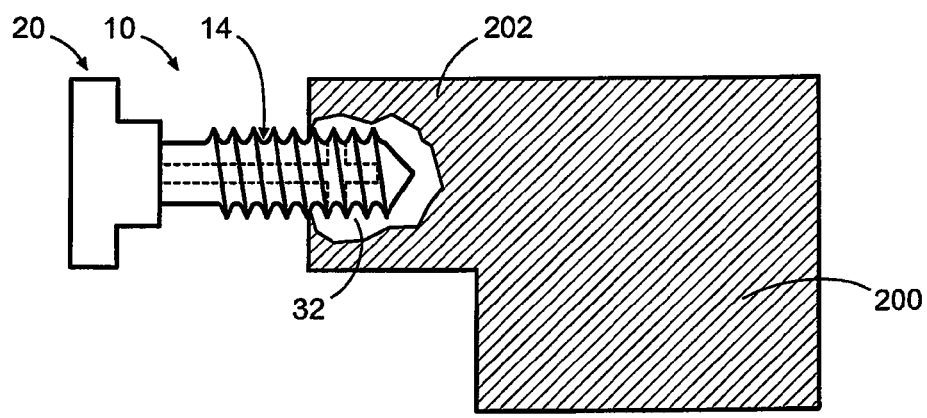
FIG. 8 illustrates a cross-section view of a method of use of the embodiment of the flexible tap apparatus member illustrated in FIG. 3.

FIG. 8 illustrates a method of use of the tap apparatus member 10 illustrated in FIG. 3. The flexible tap apparatus member 10 engages a pedicle 202 of a vertebral body 200. The handle 20 is releasably fixed to the lower shaft portion 18 of the tap apparatus member 10 at the engagement portion 22 of the handle 20. The tap apparatus member 10 is introduced to the pedicle 202 by applying pressure to the handle 20 at the grip 24. Tap apparatus members 10 increasing in dimension as desired are successively introduced in a similar manner. As each tap apparatus member 10 is introduced to the pedicle 202 the passage in the pedicle 202 slightly broadened and/or deepened. At any step during this method of use, dye 32, or another desired material, is introduced into the passage 13 disposed axially into the tap apparatus member 10. Dye 32 can be introduced by removal of the handle 20 from the tap apparatus member 10 thereby exposing the opening of the passage 13. In another embodiment, the handle 20 includes a passage (not shown) disposed therethrough arranged and configured to align with the passage 13 of the tap apparatus member 10 through which dye 32 can be introduced. Dye 32 is communicated from the axial passage 13 to the lateral passages 15 and introduced to the tissue.

In any one system 100 being implement, the tap apparatus members 10 assembled to comprise the system 100 can be uniformly one embodiment of tap apparatus member 10 (e.g. all cannulated with a center passage 13 as illustrated in FIG. 2) or a mixture of tap apparatus member 10 embodiments.

It should be emphasized that the above-described embodiments of the present invention, particularly, a "preferred" embodiment, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A method of creating a passage in tissue comprising:
    providing a flexible tap apparatus system comprising:
        a first flexible tap apparatus member, comprising:
        a shaft having a first passage disposed axially therein, a lateral passage extending laterally from said first passage to an outer surface of said shaft, a flexible upper shaft portion, and a flexible lower shaft portion;
        said upper shaft portion comprising ridges and said lower shaft portion having a substantially smooth surface; and
        a dye;
    disposing a guide pin into the tissue;
    engaging said first flexible tap apparatus member with said guide pin;
    boring a passage in the tissue with said first flexible tap apparatus member;
    communicating said dye to the tissue through said first passage and said lateral passage of said first flexible tap apparatus member;
    removing said first flexible tap apparatus member from the tissue;
    engaging a second flexible tap apparatus member with said guide pin; and
    boring into said passage in the tissue with said second flexible tap apparatus member.

2. The method of claim 1, wherein said first flexible tap apparatus member comprises a tip terminating said upper shaft portion.

3. The method of claim 1, wherein said first passage extends a portion of the length of the shaft.

4. The method of claim 1, wherein said first flexible tap apparatus member comprises a handle arranged and configured to releasably receive said lower shaft portion.

* * * * *